United States Patent [19]

Mazour et al.

[11] 4,111,974

[45] Sep. 5, 1978

[54] PROCESS FOR THE PRODUCTION OF ALKOXY-β-HALOGENOETHYLSILANES

[75] Inventors: Zdenek Mazour, Frenkendorf; Francis Louis Dayer, Basel, both of Switzerland

[73] Assignee: Ciba-Geigy Corporation, Ardsley, N.Y.

[21] Appl. No.: 763,458

[22] Filed: Jan. 28, 1977

[51] Int. Cl.² ............................................. C07F 7/18
[52] U.S. Cl. .......................................... 260/448.8 R
[58] Field of Search ................................ 260/448.8 R

[56] References Cited

U.S. PATENT DOCUMENTS 3,646,087  2/1972  Bennett et al. ............ 260/448.8 R X

OTHER PUBLICATIONS

Noll, "Chemistry and Technology of Silicones", Academic Press Inc., N.Y. (1968), pp. 81 and 82.

*Primary Examiner*—Paul F. Shaver
*Attorney, Agent, or Firm*—Karl F. Jorda

[57] ABSTRACT

A process for the production of trialkoxy-β-halogenoethylsilanes and dialkoxy-methyl-β-halogenoethylsilanes by reaction of a corresponding β-halogenoethyltrichlorosilane or β-halogenoethyl-methyldichlorosilane with an alcohol in the presence of ammonia is disclosed. The trialkoxy-β-halogenoethylsilanes and dialkoxy-methyl-β-halogenoethylsilanes obtained by this process are active substances for regulating plant growth.

12 Claims, No Drawings

PROCESS FOR THE PRODUCTION OF ALKOXY-β-HALOGENOETHYLSILANES

The present invention relates to a process for the production of alkoxy-β-halogenoethylsilanes of the formula I $$X-CH_2-CH_2-\underset{\underset{OR_1}{|}}{\overset{\overset{OR_1}{|}}{Si}}-R_2 \quad (I)$$

wherein
X represents chlorine or bromine,
$R_1$ represents a straight-chain or branched-chain alkyl group having 1 to 18 carbon atoms, an alkoxyalkyl group having 3 to 14 carbon atoms, the benzyl group or a benzyl group mono- or disubstituted by an alkoxy group having 1-4 carbon atoms, and
$R_2$ represents methyl or $R_1O-$,
by reaction of a β-halogenoethylchlorosilane of the formula II $$X-CH_2-CH_2-\underset{\underset{Cl}{|}}{\overset{\overset{Cl}{|}}{Si}}-R'_2 \quad (II)$$

wherein $R'_2$ represents methyl or chlorine and X has the meaning given under formula I, with an alcohol of the formula III $$R_1OH \quad (III)$$

wherein $R_1$ has the meaning given under formula I.

Alkoxy-β-halogenoethylsilanes of the formula I are active substances for regulating plant growth. Such active substances and their application are described, for example, in the U.S. Pat. Nos. 3,912,493 and 3,985,780, and in the U.S. patent application No. 709,827, filed July 29, 1976; or in the British patent specification No. 1,396,375.

It is known to produce alkoxy-β-halogenoethylsilanes of the formula I by reaction of β-halogenoethylchlorosilanes of the formula II with a corresponding alcohol. This process is unfavourable not only in that it gives poor yields seldom exceeding 50% of theory (see J. Org. Chem. 16, 391–394 (1951)), but also in that it is dangerous on account of the splitting-off of ethylene frequently occurring spontaneously; so that the process is useless for the commercial production of alkoxy-β-halogenoethylsilanes of the formula I.

It is also known to perform the reaction of β-halogenoethylchlorosilanes of the formula II with alcohols derived from the radical $R_1$ according to the above definition, in the presence of an acid-binding agents, especially in the presence of tertiary amines, e.g. triethylamine, pyridine or dialkylanilines (see U.S. Pat. Nos. 3,985,780 and 3,912,493, as well as British patent specification No. 1,396,375). As a result of the presence of an acid-binding agent, the spontaneous splitting-off of ethylene and the danger of explosion associated therewith are certainly avoided, but it is difficult to completely separate from the final product the employed base, in the form of the hydrochloride, by filtration and distillation of the filtrate. There is therefore obtained with this procedure a final product which is contaminated by the salt of the base used as the acid-binding agent. This is disadvantageous and disturbing particularly in the formulation of the active substances.

It is further known to react alkyltrichlorosilanes and dialkyldichlorosilanes with ammonia. There are obtained in this case however, instead of the alkyltriaminosilanes and dialkyldiaminosilanes to be expected, always only higher-molecular products. On reaction of alkyltrichlorosilanes with ammonia there are obtained silsesquizanes according to the following equation:

$$alkyl-\underset{\underset{Cl}{|}}{\overset{\overset{Cl}{|}}{Si}}-Cl + 4,5\ NH_3 \longrightarrow \frac{1}{n}\ [alkyl-Si\ (NH)_{1.5}]_n + 3NH_4Cl$$

These silsesquiazanes are obtained in yields of 25 to 56% of theory (see K. A. Adrianov et al. Zh. Obsh. Khim. 35, 2176–2180 (1965)).

The reaction of dialkyltrichlorosilane with ammonia yields cyclic products which have been called alkylcyclosilazanes. By reaction for example of dimethyldichlorosilane with ammonia in benzene at −10° C., with a reaction time of 28 hours, it was possible to obtain cyclosilazanes (tri- and tetrasilazane) in a total amount of 83.5% of theory (see U. Wannagat et al., Mh. Chem. 95, 801–811 (1964)). Such hexaalkylcyclotrisilazanes and Octaalkylcyclotetrasilazanes can be converted by reaction with alcohols into dialkoxydialkylsilanes. In the case of this reaction, the yields are, depending on the alkyl radical, between 25 and 80% of theory (see K. A. Adrianov et al., Zh. Obsh. Khim. 31, 4038–4042 (1961) and ibit. 32, 2316–2318 (1962)). The production of dialkoxy-dialkylsilanes in this manner, namely by reaction of dialkyldichlorosilanes with ammonia and subsequent alcoholysis of the formed alkylcyclosilazanes, is complicated since the process comprises two stages. Furthermore, as is shown in the aforementioned literature, the yields that are expected in this two-stage process are at best about 65% of theory. This process is therefore not suitable for the commercial production of dialkoxydialkylsilanes.

The underlying object of the present invention is hence to provide a process by which it is possible to produce dialkoxy-β-halogenoethylsilanes of the formula I in a simple manner, without safety risk, in a pure form and in good yields.

The process according to the invention for the production of alkoxy-β-halogenoethylsilanes of the formula I comprises carrying out the reaction of a β-halogenoethylchlorosilane of the formula II with an alcohol of the formula III in the presence of ammonia.

The reaction, according to the invention, of a β-halogenoethylchlorosilane of the formula II with an alcohol of the formula III is advantageously performed in an organic solvent. In general suitable are those solvents which on the one hand are inert to the starting and final products, and which on the other hand do not dissolve ammonium chloride. Furthermore, the solvent is to be so selected that the boiling point of the solvent differs sufficiently from the boiling point of the final product to render possible separation by distillation. Suitable solvents are, for example, aromatic and aliphatic hydrocarbons, such as benzene, toluene, xylene, pentane, hexane, ligroin and cyclohexane. It is also possible to use halogenated hydrocarbons, such as chlorobenzene or carbon tetrachloride.

The reaction of a β-halogenoethylchlorosilane of the formula II with an alcohol of the formula III is performed according to the present invention at temperatures between −30° and +80° C. The reaction is preferably performed between −10° and +30° C. An advantageous procedure is to bring the constituents together at a temperature at the lower limit of the given temperature range, and to then move to a temperature at the upper limit of the given range.

The ammonia is added in at least the stoichiometric amount, i.e. there is added per chlorine atom to be substituted at least 1 mole of ammonia. The amount of ammonia to be added according to the invention is 1.0 to 1.25 moles per chlorine atom to be substituted, preferably 1.0 to 1.1 moles per chlorine atom to be substituted.

For the reaction of a β-halogenoethylchlorosilane of the formula II with an alcohol of the formula III, there are essentially used stoichiometric amounts of the reactants, i.e. there is essentially used 1 mole of alcohol of the formula III per chlorine atom to be substituted. According to the present invention, it has proved advantageous to use 0.95 to 1.25 moles, preferably 1.0 to 1.1 moles, of alcohol of the formula III per chlorine atom to be substituted.

An advantageous embodiment of the process according to the invention comprises firstly introducing ammonia into a solution of a β-halogenoethylchlorosilane of the formula II in a solvent and subsequently adding immediately an alcohol of the formula III.

According to a further advantageous embodiment, the alcohol of the formula III is added simultaneously with the ammonia to the solution of the β-halogenoethylchlorosilane of the formula II in an inert solvent.

In further processing of the reaction mixture, the formed ammonium chloride is filtered off and the solvent is distilled off from the filtrate. The removal of the solvent by distillation is advantageously performed in vacuo. The crude alkoxy-β-halogenoethylsilane of the formula I, obtained as distillation residue, is already of high purity and for many purposes it can be used directly. If necessary, it is purified by distillation.

The radical $R_1$ as an alkoxyalkyl group having 3 to 14 carbon atoms comprises preferably alkoxyalkyl groups having 2 to 3 carbon atoms in the alkyl group and 1 to 12 carbon atoms, preferably 1 to 4 carbon atoms, in the alkoxy group. Particularly preferred alkoxyalkyl groups are the 2-methoxyethyl group, the 2-methoxypropyl group and the 3-methoxypropyl group.

The process according to the invention is suitable in particular for the production of alkoxy-β-halogenoethylsilanes of the formula I wherein $R_1$ represents an alkyl group having 1 to 5 carbon atoms, preferably 1 to 3 carbon atoms, the β-methoxyethyl group or the benzyl group, and the alkyl groups can be straight-chain or branched-chain. Preferred alkoxy-β-halogenoethylsilanes of the formula I are, for example, triethoxy-β-halogenoethylsilane, tris-(β-methoxyethoxy)-β-chloroethylsilane, diethoxy-β-chloroethylmethylsilane and dibenzyloxy-β-chloroethylmethylsilane.

With the process according to the invention, it is possible to produce the alkoxy-β-halogenoethylsilanes of the formula I with the avoidance of all risk to safety, in a simple manner, in high yields and with a high degree of purity. Not only the yields but also the purity of the resulting alkoxy-β-halogenoethylsilanes of the formula I are higher than those obtained by the initially mentioned processes known hitherto. The purity of the alkoxy-β-halogenoethylsilanes of the formula I produced by the process according to the invention is to be attributed in particular to the fact that the ammonium chloride formed as by-product can be separated practically quantitatively from the reaction mixture.

In view of prior knowledge of the reaction of alkyltrichlorosilanes and dialkyldichlorosilanes with ammonia, whereby there were always employed at least 1.5 moles of ammonia per chlorine atom to be substituted, it has to be considered surprising that such high yields are obtained with the procedure according to the invention. This could not have been anticipated, particularly on the basis of the results described in connection with the reaction of hexaalkylcyclotrisilazanes and octaalkylcyclotetrasilazanes with alcohol (see U. Wannagat et al., MH. Chem. 95, 801–811, (1964)).

The process according to the invention is further illustrated by the following Examples.

EXAMPLE 1

Triethoxy-β-chloroethylsilane

A solution of 99.0 g (0.5 mole) of β-chloroethyltrichlorosilane in 500 ml of ligroin (b.p.$_{760}$ = 80°–110° C.) is cooled with stirring to −10° C. Into the clear colourless solution is introduced, below the surface, 28.05 g (1.65 moles) of gaseous ammonia with further cooling to ensure that the temperature does not exceed +5° C. Immediately after the addition of ammonia is completed, there is added dropwise to the formed white suspension 75.9 g (1.65 moles) of absolute ethanol, whereupon the temperature rises to +8° C. The reaction mixture is subsequently stirred at 20°–25° C. for a further 12 hours. The whole mixture is then cooled to −5° C.; it is stirred for half an hour at this temperature; the ammonium chloride is filtered off and washed on the filter three times with 100 ml of cold ligroin each time. The ligroin is completely distilled off at 20°–45° C. under 12–15 mm Hg from the combined colourless filtrates. As residue is obtained 105.7 g (93.2% of theory) of crude triethoxy-β-chloroethylsilane, which consists according to gas-chromatographic analysis to the extent of 96.5% of triethoxy-2-chloroethylsilane (90% of theory relative to employed 2-chloroethyltrichlorosilane).

EXAMPLE 2

Triethoxy-β-chloroethylsilane 27.65 g (0.6 mole) of absolute ethanol and 10.5 g (0.6 mole) of gaseous ammonia are introduced simultaneously, with stirring and cooling, into a solution (cooled to −10° C.) of 35.7 g (0.18 mole) of β-chloroethyltrichlorosilane in 160 g of toluene, the addition being made in such a way that the temperature does not exceed +5° C. After removal of the cooling bath, the white suspension formed is stirred for 12 hours at room temperature. The whole of the mixture is then cooled to −5° C. and stirred for half an hour at this temperature; the ammonium chloride formed during the reaction is filtered off and washed on the filter three times with 50 ml of cold toluene each time. The toluene is completely distilled off at 60° C. under 12–15 mm Hg from the clear combined filtrates. As residue is obtained 36.8 g (86.3% of theory) of crude triethoxy-β-chloroethylsilane, which consists to the extent of 98% of triethoxy-β-chloroethylsilane. The net yield is accordingly 84.6% of theory.

EXAMPLE 3

Diethoxy-β-chloroethylmethylsilane 8.5 g (0.5 mole) of gaseous ammonia is introduced into a solution (cooled to −5° C.) of 44.4 g (0.25 mole) of β-chloroethylmethyldichlorosilane in 300 ml of toluene, with stirring and cooling to ensure that the temperature does not exceed +5° C. Immediately after completion of the ammonia addition, there is added dropwise to the suspension formed 23.0 g (0.5 mole) of absolute ethanol, whereupon the temperature rises to −2° C. After removal of the cooling bath, the whole of the mixture is stirred at 20°-25° C. for a further 14 hours; it is subsequently cooled to −5° C. and stirred for half an hour at this temperature. The ammonium chloride formed during the reaction is then filtered off and washed on the filter with cold toluene. The washing toluene is combined with the filtrate and the toluene is distilled off at 50° C. under 12 mm Hg. The crude diethoxy-β-chloroethylmethylsilane obtained as residue is purified by vacuum distillation. There is obtained 43.5 g (88.4% of theory) of diethoxy-β-chloroethylmethylsilane of boiling point 76°-77° C./10 mm Hg. According to gas-chromatographic analysis, the product consists to the extent of 96% of diethoxy-β-chloroethylmethylsilane. From this content is calculated a net yield of 84.9% of theory relative to the employed β-chloroethylmethyldichlorosilane.

EXAMPLE 4

Tripropoxy-β-chloroethylsilane 8.41 g (0.495 mole) of gaseous ammonia is introduced into a solution (cooled to −10° C.) of 29.7 g (0.15 mole) of β-chloroethyltrichlorosilane in 150 ml of toluene, with stirring and cooling being maintained in a manner ensuring that the temperature does not exceed +5° C. Directly after the addition of ammonia is completed, the cooling bath is removed and 29.75 g (0.495 mole) of anhydrous n-propanol is added dropwise at 25°-30° C. to the white suspension. The reaction mixture is subsequently stirred at 25°-30° C. for a further 12 hours; it is then cooled to −5° C. and stirred for a further half hour at this temperature; the ammonium chloride formed during the reaction is filtered off and washed three times with 50 ml of cold toluene each time. The washing toluene is combined with the filtrate and the toluene is completely distilled off under 10-12 mm Hg, with the bath temperature rising to 70° C. The crude tripropoxy-β-chloroethylsilane obtained as residue is purified by vacuum distillation to obtain 32.6 g (80.8% of theory) of tripropoxy-β-chloroethylsilane having a boiling point of 119°-120° C./15 mm Hg. According to gas-chromatographic analysis, the product contains 99% of tripropoxy-β-chloroethylsilane. From this is calculated a net yield of 80.5% of theory, relative to employed β-chloroethyltrichlorosilane.

EXAMPLE 5

Diethoxy-β-bromoethylmethylsilane 34.13 g (0.742 mole) of absolute ethanol and 12.61 g (0.742 mole) of gaseous ammonia are introduced simultaneously, with stirring and cooling, into a solution (cooled to −6° C.) of 79.9 g (0.36 mole) of β-bromoethylmethyldichlorosilane in 200 ml of toluene, the addition being made in such a way that the temperature does not exceed +5° C. After removal of the cooling bath, the white suspension formed is subsequently stirred at room temperature for 12 hours. The mixture is then cooled to −5° C. and stirred at this temperature for half an hour; the ammonium chloride is filtered off and washed three times on the filter with 50 ml of cold toluene each time. The washing toluene is combined with the filtrate and the toluene is distilled off at 40°-45° C. under 13-15 mm Hg. The crude diethoxy-β-bromoethylmethylsilane obtained as residue is purified by vacuum distillation to obtain 74.0 g (85.2% of theory) of diethoxy-β-bromoethylmethylsilane having a boiling point of 84°-85° C./12-13 mm Hg. According to gas-chromatographic analysis, the product contains 89% of diethoxy-β-bromoethylmethylsilane. From this content is calculated a net yield of 75.9% of theory.

EXAMPLE 6

Bis-(benzyloxy)-β-chloroethyl-methylsilane 324.4 g (3.0 moles) of benzyl alcohol and 56.1 g (3.3 moles) of gaseous ammonia are introduced simultaneously, with stirring and cooling, into a solution (cooled to −8° C.) of 267.7 g (1.5 moles) of β-chloroethylmethyldichlorosilane in 2100 ml of toluene, the addition being made in such a way that the temperature does not exceed +5° C. After removal of the cooling bath, the formed white suspension is then stirred at 20°-25° C. for 16 hours. The mixture is subsequently cooled to −5° C. and stirred for half an hour at this temperature; the ammonium chloride formed during the reaction is filtered off and washed three times with 200 ml of cold toluene each time. The washing toluene is combined with the colourless filtrate, and the toluene is distilled off at 40°-50° C. under 13-15 mm Hg. The residual toluene is removed at 60° C. under 0.02 to 0.03 mm Hg from the crude bis-(benzyloxy)-β-chloroethyl-methylsilane obtained. There is thus obtained 417 g (86.2% of theory) of bis-(benzyloxy)-β-chloroethyl-methylsilane. The product contains according to gas-chromatographic analysis 99.2% of bis-(benzyloxy)-β-chloroethyl-methylsilane. This corresponds to a net yield of 85.5% of theory, relative to the β-chloroethylmethyldichlorosilane.

EXAMPLE 7

Tris-(2-methoxyethoxy)-β-chloroethylsilane 37.62 g (0.495 mole) of β-methoxyethanol and 8.41 g (0.495 mole) of gaseous ammonia are introduced simultaneously, with stirring and cooling, into a solution (cooled to −6° C.) of 29.7 g (0.15 mole) of β-chloroethyltrichlorosilane in 150 ml of toluene, the addition being made in such a way that the temperature does not exceed +5° C. The white suspension formed is subsequently stirred at 20°-25° C. for 14 hours. The mixture is then cooled to −5° C. and stirred for half an hour at this temperature; the ammonium chloride formed during the reaction is filtered off and washed on the filter three times with 50 ml of cold toluene each time. The washing toluene is combined with the filtrate and the toluene is distilled off at 40°-50° C. under 13-15 mm Hg. The residual toluene is removed at 60° C. under 0.02 to 0.03 mm Hg from the residue. There is obtained 43.0 g (90.5% of theory) of tris-(β-methoxyethoxy)-β-chloroethylsilane. According to gas-chromatographic analysis, the product contains 98.7% of tris-(β-methoxyethoxy)-β-chloroethylsilane. This corresponds to a net yield of 89.3% of theory, relative to the employed β-chloroethyltrichlorosilane.

EXAMPLE 8

Tris-(dodecyloxy)-β-chloroethylsilane 279.5 g (1.5 moles) of dodecyl alcohol and 25.5 g (1.5 moles) of gaseous ammonia are introduced simultaneously, with stirring and cooling, into a solution (cooled to 0° to +5° C.) of 99.0 g (0.5 mole) of β-chloroethyltrichlorosilane in 500 ml of toluene. The white suspension formed is subsequently stirred, after removal of the cooling bath, at 20° to 25° C. for 2 hours. The mixture is then slowly cooled to −5° to 0° C.; the ammonium chloride formed during the reaction is filtered off and washed on the filter twice with 100 ml of cold toluene each time. The washing toluene is combined with the filtrate and the toluene is evaporated off at a bath temperature of 60° C. under 12 mm Hg. To effect the complete removal of the solvent, the residue is heated for a further hour at 60° C. under 0.01–0.02 mm Hg. There is obtained 238 g (73.5% of theory) of tris-(dodecyloxy)-β-chloroethylsilane, relative to the employed β-chloroethyltrichlorosilane.

We claim:

1. Process for the production of alkoxy-β-halogenoethylsilanes of the formula I

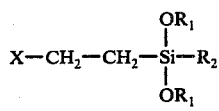

wherein
X represents chlorine or bromine,
$R_1$ represents a straight-chain or branched-chain alkyl group having 1 to 18 carbon atoms, an alkoxyalkyl group having 3 to 14 carbon atoms, the benzyl group or a benzyl group mono- or disubstituted by an alkoxy group having 1–4 carbon atoms, and
$R_2$ represents methyl or $R_1O—$,
by reaction of a β-halogenoethylchlorosilane of the formula II

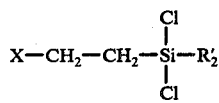

wherein $R'_2$ represents methyl or chlorine and X has the meaning given under formula I, with an alcohol of the formula III $$R_1OH \quad \text{(III)}$$

wherein $R_1$ has the meaning given under formula I, which process comprises carrying out the reaction of a β-halogenoethylchlorosilane of the formula II with an alcohol of the formula III in the presence of ammonia.

2. Process according to claim 1, wherein the reaction of a β-halogenoethylchlorosilane of the formula II with an alcohol of the formula III is performed in an organic solvent.

3. Process according to claim 1, wherein the reaction of a β-halogenoethylchlorosilane of the formula II with an alcohol of the formula III is performed in the presence of an aliphatic or aromatic hydrocarbon.

4. Process according to claim 1, wherein the reaction of a β-halogenoethylsilane of the formula II with an alcohol of the formula III is performed at temperatures of between −30° and +80° C.

5. Process according to claim 1, wherein the reaction of a β-halogenoethylchlorosilane of the formula II with an alcohol of the formula III is performed at temperatures of between −10° and +30° C.

6. Process according to claim 1, wherein 1.0 to 1.25 moles of ammonia are added per chlorine atom to be substituted.

7. Process according to claim 1, wherein 1.0 to 1.1 moles of ammonia are used per chlorine atom to be substituted.

8. Process according to claim 1, wherein β-halogenoethylsilanes of the formula II and alcohols of the formula III are used in essentially stoichiometric amounts.

9. Process according to claim 1, wherein 0.95 to 1.25 moles of alcohol of the formula III are used per chlorine atom to be substituted.

10. Process according to claim 1, wherein 1.0 to 1.1 moles of alcohol of the formula III are used per chlorine atom to be substituted.

11. Process according to claim 1, wherein firstly ammonia is introduced into a solution of a β-halogenoethylchlorosilane of the formula II in an inert solvent, and immediately afterwards an alcohol of the formula III is added.

12. Process according to claim 1, wherein ammonia and an alcohol of the formula III are added simultaneously to a solution of a β-halogenoethylchlorosilane of the formula II in an inert solvent.

* * * * *